United States Patent
Jacobs et al.

(10) Patent No.: US 9,814,614 B2
(45) Date of Patent: *Nov. 14, 2017

(54) VERTICALLY ORIENTED BAND FOR STOMACH

(71) Applicant: Advanced Bariatric Technology, LLC, Coral Gables, FL (US)

(72) Inventors: Moises Jacobs, Miami, FL (US); Moises Jacobs, III, Miami, FL (US)

(73) Assignee: Advanced Bariatric Technology, LLC, Coral Gables, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/531,300

(22) Filed: Nov. 3, 2014

(65) Prior Publication Data
US 2015/0051624 A1 Feb. 19, 2015

Related U.S. Application Data

(63) Continuation of application No. 11/984,452, filed on Nov. 19, 2007, now Pat. No. 8,920,305, which is a
(Continued)

(51) Int. Cl.
*A61F 5/00* (2006.01)
*A61B 17/122* (2006.01)

(52) U.S. Cl.
CPC .......... *A61F 5/0086* (2013.01); *A61B 17/122* (2013.01)

(58) Field of Classification Search
CPC ...... A61F 5/0083; A61F 5/0086; A61B 17/12; A61B 17/122; A61B 17/1227;
(Continued)

(56) References Cited

U.S. PATENT DOCUMENTS 3,254,651 A 6/1966 Collito
3,316,914 A 5/1967 Collito
(Continued)

FOREIGN PATENT DOCUMENTS

AU 201399422 2/2017
CN 105007838 A 10/2015
(Continued)

OTHER PUBLICATIONS

Office Action cited in U.S. Appl. No. 11/797,537 dated Jul. 16, 2009.
(Continued)

*Primary Examiner* — Charles A Marmor, II
*Assistant Examiner* — Carrie R Dorna
(74) *Attorney, Agent, or Firm* — Gardere Wynne Sewell LLP

(57) ABSTRACT

An adjustable band or clamp or non-adjustable clamp is placed about the greater curvature of the stomach in a vertical orientation. The band or clamp completely compartmentalizes the stomach between a small vertical pouch and the fundus and body of the stomach. The fundus and body of the stomach are excluded from nutrients and are separated from a long narrow channel where the food travels. A small passage at the level of the antrum allows gastric juices to empty from the fundus and body of the stomach. The clamp may be applied during open surgery in laproscopic surgery or using a single port technique, or through any natural orifice in NOTES (Natural Orifice Transluminal Endoscopic surgery) or using a hybrid surgical technique.

20 Claims, 5 Drawing Sheets

Related U.S. Application Data continuation-in-part of application No. 11/797,537, filed on May 4, 2007, now abandoned.

(60) Provisional application No. 60/881,138, filed on Jan. 19, 2007.

(58) Field of Classification Search
CPC .............. A61B 17/128; A61B 17/1285; A61B 17/0643; A61B 17/0682; A61B 17/083
USPC ................... 600/37; 604/909; 606/139, 142, 606/153–157, 191, 198; 128/897–898
See application file for complete search history.

(56) References Cited

U.S. PATENT DOCUMENTS

| | | | |
|---|---|---|---|
| 3,766,925 A | 10/1973 | Rubricius | |
| 4,060,089 A | 11/1977 | Noiles | |
| 4,274,415 A | 6/1981 | Kanamoto et al. | |
| 4,390,019 A | 6/1983 | LeVeen et al. | |
| 4,458,681 A * | 7/1984 | Hopkins | 606/157 |
| 4,548,202 A | 10/1985 | Duncan | |
| 4,558,699 A | 12/1985 | Bashour | |
| 4,610,250 A | 9/1986 | Green | |
| 4,803,985 A | 2/1989 | Hill | |
| 4,950,284 A | 8/1990 | Green et al. | |
| 4,976,721 A | 12/1990 | Blasnik et al. | |
| 5,062,846 A | 11/1991 | Oh et al. | |
| 5,074,868 A | 12/1991 | Kuzmak | |
| 5,156,609 A | 10/1992 | Nakao et al. | |
| 5,163,945 A | 11/1992 | Ortiz et al. | |
| 5,226,429 A | 7/1993 | Kuzmak | |
| 5,234,454 A | 8/1993 | Bangs | |
| 5,236,437 A | 8/1993 | Wilk et al. | |
| 5,250,058 A | 10/1993 | Miller et al. | |
| 5,327,914 A | 7/1994 | Shlain | |
| 5,345,949 A | 9/1994 | Shlain | |
| 5,456,714 A | 10/1995 | Owen | |
| 5,464,416 A | 11/1995 | Steckel | |
| 5,549,621 A | 8/1996 | Bessler et al. | |
| 5,575,802 A | 11/1996 | McQuilkin et al. | |
| 5,766,189 A | 6/1998 | Matsuno | |
| 5,901,993 A | 5/1999 | Lowery et al. | |
| 6,036,704 A | 3/2000 | Yoon | |
| 6,179,850 B1 | 1/2001 | Goradia | |
| 6,464,710 B1 | 10/2002 | Foster | |
| 6,503,258 B1 | 1/2003 | Filho | |
| 6,537,289 B1 | 3/2003 | Kayan et al. | |
| 6,572,629 B2 | 6/2003 | Kalloo et al. | |
| 6,694,982 B2 | 2/2004 | Latour | |
| 6,716,226 B2 | 4/2004 | Sixto, Jr. et al. | |
| 6,814,742 B2 | 11/2004 | Kimura et al. | |
| 6,869,438 B2 | 3/2005 | Chao | |
| 6,926,724 B1 | 8/2005 | Chu | |
| 6,981,978 B2 | 1/2006 | Gannoe | |
| 7,022,126 B2 | 4/2006 | De Canniere | |
| 7,105,000 B2 | 9/2006 | McBrayer | |
| 7,135,032 B2 | 11/2006 | Akerfeldt | |
| 7,214,233 B2 | 5/2007 | Gannoe et al. | |
| 7,223,229 B2 | 5/2007 | Inman et al. | |
| 7,232,445 B2 | 6/2007 | Kortenbach et al. | |
| 7,261,725 B2 | 8/2007 | Binmoeller | |
| 7,288,100 B2 | 10/2007 | Molina Trigueros | |
| 7,320,701 B2 | 1/2008 | Haut et al. | |
| 7,338,503 B2 | 3/2008 | Rosenberg et al. | |
| 7,416,528 B2 | 8/2008 | Crawford et al. | |
| 7,645,285 B2 | 1/2010 | Cosgrove et al. | |
| 7,691,053 B2 | 4/2010 | Viola | |
| 7,758,493 B2 | 7/2010 | Gingras | |
| 7,871,416 B2 | 1/2011 | Phillips | |
| 7,892,244 B2 | 2/2011 | Monassevitch et al. | |
| 8,287,559 B2 | 10/2012 | Barker et al. | |
| 8,382,775 B1 | 2/2013 | Bender et al. | |
| 8,529,585 B2 | 9/2013 | Jacobs et al. | |
| 8,920,305 B2 | 12/2014 | Jacobs et al. | |
| 2002/0022851 A1 | 2/2002 | Kalloo et al. | |
| 2002/0082625 A1 | 6/2002 | Huxel et al. | |
| 2002/0138086 A1 | 9/2002 | Sixto et al. | |
| 2004/0082963 A1 | 4/2004 | Gannoe et al. | |
| 2004/0097989 A1 | 5/2004 | Molina Trigueros | |
| 2004/0116945 A1 | 6/2004 | Sharkawy et al. | |
| 2005/0119674 A1 | 6/2005 | Gingras | |
| 2005/0125014 A1 | 6/2005 | Duluco et al. | |
| 2005/0149069 A1 | 7/2005 | Bertolero et al. | |
| 2005/0197714 A1 * | 9/2005 | Sayet | 623/23.65 |
| 2005/0216042 A1 | 9/2005 | Gertner | |
| 2005/0250980 A1 | 11/2005 | Swanstrom et al. | |
| 2005/0251158 A1 | 11/2005 | Saadat et al. | |
| 2005/0277959 A1 | 12/2005 | Cosgrove et al. | |
| 2006/0074440 A1 | 4/2006 | Garner | |
| 2006/0157067 A1 | 7/2006 | Saadat et al. | |
| 2006/0217757 A1 | 9/2006 | Horndeski | |
| 2006/0252983 A1 | 11/2006 | Lembo et al. | |
| 2006/0264981 A1 | 11/2006 | Viola | |
| 2006/0264982 A1 | 11/2006 | Viola et al. | |
| 2006/0264987 A1 | 11/2006 | Sgro | |
| 2007/0021761 A1 * | 1/2007 | Phillips | 606/157 |
| 2007/0032807 A1 | 2/2007 | Ortiz et al. | |
| 2007/0149989 A1 | 6/2007 | Santilli et al. | |
| 2007/0167962 A1 | 7/2007 | Gannoe et al. | |
| 2007/0213747 A1 | 9/2007 | Monassevitch et al. | |
| 2007/0265644 A1 | 11/2007 | Ichihara et al. | |
| 2008/0033457 A1 | 2/2008 | Francischelli et al. | |
| 2008/0039879 A1 | 2/2008 | Chin et al. | |
| 2008/0082114 A1 | 4/2008 | McKenna et al. | |
| 2008/0092910 A1 | 4/2008 | Brooks | |
| 2008/0177292 A1 | 7/2008 | Jacobs et al. | |
| 2008/0208324 A1 | 8/2008 | Glithero et al. | |
| 2008/0275480 A1 | 11/2008 | Jacobs et al. | |
| 2008/0287976 A1 | 11/2008 | Weaner et al. | |
| 2008/0319435 A1 | 12/2008 | Rioux et al. | |
| 2009/0137870 A1 | 5/2009 | Bakos et al. | |
| 2009/0138009 A1 | 5/2009 | Viswanathan et al. | |
| 2009/0198266 A1 | 8/2009 | Cesare | |
| 2010/0030017 A1 | 2/2010 | Baker et al. | |
| 2011/0046641 A1 | 2/2011 | Kassab et al. | |
| 2011/0092993 A1 | 4/2011 | Jacobs | |
| 2011/0092998 A1 | 4/2011 | Hirszowicz et al. | |
| 2011/0098732 A1 | 4/2011 | Jacobs | |
| 2011/0190791 A1 | 8/2011 | Jacobs et al. | |
| 2012/0095484 A1 | 4/2012 | Dominguez | |
| 2012/0123463 A1 | 5/2012 | Jacobs | |
| 2014/0046345 A1 | 2/2014 | Armenteros et al. | |
| 2014/0074131 A1 | 3/2014 | Armenteros et al. | |
| 2017/0258619 A1 | 9/2017 | Jacobs et al. | |

FOREIGN PATENT DOCUMENTS

| | | |
|---|---|---|
| CN | 107072660 A | 8/2017 |
| CO | 30415 | 12/2016 |
| DE | 19751733 A1 | 12/1998 |
| DE | 29822558 U1 | 2/1999 |
| EP | 0201344 A2 | 11/1986 |
| EP | 0220643 A2 | 5/1987 |
| EP | 1397998 A1 | 3/2004 |
| EP | 1547529 A1 | 6/2005 |
| EP | 1600108 A2 | 11/2005 |
| EP | 1749506 A1 | 2/2007 |
| EP | 1806101 A1 | 7/2007 |
| EP | 1882451 A2 | 1/2008 |
| EP | 3185784 A1 | 7/2017 |
| JP | 9289989 A | 11/1997 |
| JP | 2002085414 A | 3/2002 |
| JP | 2007044517 A | 2/2007 |
| JP | 2007097664 A | 4/2007 |
| JP | 2007159794 A | 6/2007 |
| RU | 2386455 C2 | 4/2010 |
| TH | 158414 | 12/2016 |
| WO | WO-98/33437 | 8/1998 |
| WO | WO-99/11179 | 3/1999 |
| WO | WO-00/76432 | 12/2000 |
| WO | WO-00/78234 | 12/2000 |
| WO | WO-02/064041 | 8/2002 |
| WO | WO-2004/017839 | 3/2004 |

(56) References Cited

FOREIGN PATENT DOCUMENTS

| WO | WO-2006/033385 | 3/2006 |
|---|---|---|
| WO | WO-2007/013995 | 2/2007 |
| WO | WO-2008/081436 | 7/2008 |
| WO | WO-2008/091537 | 7/2008 |
| WO | WO-2008/101048 | 8/2008 |
| WO | WO-2011/094700 | 8/2011 |
| WO | WO-2016/033221 A1 | 3/2016 |

OTHER PUBLICATIONS

Office Action cited in U.S. Appl. No. 11/797,537 dated Jan. 7, 2010.
Office Action cited in U.S. Appl. No. 11/984,452, dated Aug. 5, 2009.
Final Office Action cited in U.S. Appl. No. 11/984,452, dated Mar. 26, 2010.
Examiner's Interview Summary cited in U.S. Appl. No. 11/984,452, dated Jun. 11, 2010.
Office Action cited in U.S. Appl. No. 11/984,452, dated Aug. 6, 2012.
Final Office Action cited in U.S. Appl. No. 11/984,452, dated Jan. 31, 2013.
Office Action cited in U.S. Appl. No. 11/984,452, dated May 20, 2013.
Copending U.S. Appl. No. 13/963,998, filed Aug. 9, 2013; Inventors: Jesus R. Armenteros et al.
Copending U.S. Appl. No. 14/021,720, filed Sep. 9, 2013; Inventors: Jesus R. Armenteros et al.
PCT International Search Report cited in Patent Application No. PCT/US2008/000644, dated Jul. 7, 2008.
International Preliminary Report on Patentability cited in PCT/US2008/000644, dated Nov. 17, 2009.
Written Opinion cited in PCT/US2008/000644, dated Jul. 7, 2008.
PCT International Search Report and Written Opinion cited in Patent Application No. PCT/US2011/023205, dated Apr. 5, 2011.
International Preliminary Report on Patentability cited in PCT/US2011/023205, dated Jul. 31, 2012.
Copending International Patent Application No. PCT/US2013/54435 filed Aug. 9, 2013; First Named Inventor: Armenteros, Jesus R.
International Search Report cited in PCT/US2013/54435, dated Jan. 16, 2014.
Written Opinion cited in PCT/US2013/54435 dated Jan. 16, 2014.
Helmut Kapczynski, Surgical Instruments 101, An Introduction to Kmedic Certified Instruments, Kmedic, Inc., 1997, Northvale, New Jersey.
An espace English abstract of JP-9289989-A (Nov. 11, 1997).
Patent Abstract of Japan of JP-2002085414-A (Mar. 26, 2002).
Patent Abstract of Japan of JP-2007044517-A (Feb. 22, 2007).
An espace English abstract of JP-2007097664-A (Apr. 19, 2007).
An espace English abstract of JP-2007159794-A (Jun. 28, 2007).
An espace English abstract of DE-19751733 (Dec. 10, 1998).
Communication and Supplementary European Search Report of EP Application No. EP11737828, Sep. 23, 2014.
Machine Translation of DE29822558 U1 (Feb. 18, 1999).
Copending U.S. Appl. No. 62/042,117, filed Aug. 26, 2014; first named inventor: Jesus R. Armenteros.
Response to Office Action in U.S. Appl. No. 11/984,452 dated Oct. 3, 2013.
Final Office Action cited in U.S. Appl. No. 11/984,452 dated Jan. 30, 2014.
RCE and Response to Final Office Action in U.S. Appl. No. 11/984,452, dated May 30, 2014.
Applicant-Initiated Interview Summary in U.S. Appl. No. 11/984,452, dated May 30, 2014.
Notice of Allowance in U.S. Appl. No. 11/984,452 mailed Jun. 30, 2014.
International Preliminary Report on Patentability cited in PCT/US2013/054435, dated Jun. 9, 2015 (9 pgs).
Office Action for U.S. Appl. No. 14/021,720 dated Oct. 7, 2014 (6 pgs).
Response to Office Action for U.S. Appl. No. 14/021,720 dated Dec. 3, 2014 (8 pgs).
Office Action for U.S. Appl. No. 14/021,720 dated Jan. 2, 2015 (8 pgs).
Response to Office Action for U.S. Appl. No. 14/021,720 dated Apr. 2, 2015 (13 pgs).
Copending U.S. Appl. No. 62/118,455, filed Feb. 19, 2015; first named inventor: Jesus R. Armenteros.
Office Action for U.S. Appl. No. 14/021,720 dated Jun. 12, 2015 (9 pgs).
Response to Office Action for U.S. Appl. No. 14/021,720 dated Oct. 12, 2015 (10 pgs).
Examiner initiated Interview Summary, Advisory Action, and AFCP 2.0 Decision in U.S. Appl. No. 14/021,720, dated Oct. 29, 2015 (7 pgs).
Copending U.S. Appl. No. 14/836,621, filed Aug. 26, 2015; First-Named Inventor: Jesus R. Armenteros.
Copending International Patent Application No. PCT/US2015/47005 filed Aug. 26, 2015; First Named Inventor: Moises Jacobs.
Jacobs, Moises, et al., Presentation, "A Novel Procedure for Bariatric and Metabolic Surgery, a weight loss clamp" Apr. 2015 (20 pgs).
"A Pathway to Endoscopic Bariatric Therapies" Gastrointestinal Endoscopy Journal, www.giejournal.org, vol. 74, No. 5 (2011), pp. 943-953.
Search Report of copending Singapore Application No. SG11201500782R, dated Oct. 8, 2015.
Written Opinion of copending Singapore Application No. SG11201500782R, dated Oct. 12, 2015.
International Search Report and Written Opinion of PCT/US2015/047005, Nov. 27, 2015.
Office Action for U.S. Appl. No. 14/531,300 dated Oct. 19, 2015 (7 pages).
Advisory Action and Interview Summary for U.S. Appl. No. 14/021,720 dated Oct. 27, 2016 (5 pgs).
Communication Pursuant to Article 94(3) EPC from EPO in EP Application No. EP11737828, Jun. 8, 2016, 6 pgs.
Examiner's Report dated Oct. 21, 2015 in AU Application No. 2013299422, 3 pgs.
Final Office Action for U.S. Appl. No. 14/021,720 dated Jul. 14, 2016 (14 pgs).
First Examination Report of New Zealand Patent Application 704680, dated May 20, 2016, 6 pgs.
Geoffrey W.J. Vertical Ligated Gastroplasty by Clamp, Cut and Suture: A Series of 504 Cases Dating Back to 1977. Obes Surg. Nov. 1994;4(4):344-348, PMID: 10742799 [PubMed—as supplied by publisher], 5 pgs.
Notice of Allowance for U.S. Appl. No. 14/021,720 dated Dec. 27, 2016 (8 pgs).
Office Action for U.S. Appl. No. 13/963,998 dated Nov. 15, 2016 (13 pgs).
Office Action in Canadian Application No. 2880155, dated Feb. 17, 2016, 5 pgs.
Office Action in Canadian Application No. 2880155, dated Nov. 23, 2016, 4 pgs.
Office Action in Chinese Patent Application No. 2013800523046, (dated Dec. 19, 2016), 9 pgs.
Office Action in Columbian Patent Application No. 15053467, (dated Jul. 21, 2016), 7 pgs.
Office Action Restriction Requirement for U.S. Appl. No. 13/963,998 dated Jun. 1, 2016 (8 pgs).
Office Action, Translation and Search Report in Russian Patent Application No. 2015108054, (dated May 27, 2016), 6 pgs.
Office Action, Translation and Search Report in Russian Patent Application No. 2015108054, (dated Oct. 26, 2016), 6 pgs.
Response to Advisory Action for U.S. Appl. No. 14/021,720 dated Nov. 10, 2016 (9 pgs).
Response to Communication Pursuant to Article 94(3) EPC from EPO in EP Application No. EP11737828, dated Dec. 19, 2016, 19 pgs.

(56) References Cited

OTHER PUBLICATIONS

Response to Examiner's Report dated Oct. 21, 2015 in AU Application No. 2013299422, (dated Jul. 8, 2016), 31 pgs.
Response to Final Office Action for U.S. Appl. No. 14/021,720 dated Oct. 13, 2016 (9 pgs).
Response to First Examination Report of New Zealand Patent Application 704680, dated Dec. 19, 2016, 3 pgs.
Response to Office Action in Canadian Application No. 2880155, dated Aug. 17, 2016, 4 pgs.
Response to Office Action Restriction Requirement for U.S. Appl. No. 13/963,998 dated Jul. 7, 2016 (16 pgs).
Response to Russian Office Action in Application No. 2015108054, (dated Aug. 30, 2016), 1 pg.
Response to Written Opinion of copending Singapore Application No. SG11201500782R, dated Mar. 31, 2016, 6 pgs.
Supplementary European Search Report in EP Application No. EP13828055.7, dated Aug. 31, 2016, 5 pgs.
ШАЛИМОВ А.А. и др., Хирургия пищеварительного тракта. Киев "Здоров'я", ", 1987, c.558. Document not available, translation not available, Search Report in Russian Patent Application No. 2015108054, (dated May 27, 2016).
Copending U.S. Appl. No. 62/359,529, filed Jul. 7, 2016; first named inventor: Jesus R. Armenteros.
Notice of Acceptance in AU Application No. 2013299422, (dated Nov. 1, 2016), 2 pgs.
Response to Russian Office Action in Application No. 2015108054, (dated Jan. 26, 2017), 1 pg.
Further Examination Report of New Zealand Patent Application 704680, dated Jan. 24, 2017, 3 pgs.
Response to Office Action t for U.S. Appl. No. 13/963,998 dated Nov. 15, 2016, filed Feb. 10, 2017 (18 pgs).
Request for Substantive Examination and Claim Amendments in BR Application No. BR 112015 0027253, (dated Jul. 11, 2016), 13 pgs.
Response Brief filed in Columbian Patent Application No. 15053467, (dated Sep. 22, 2016), 6 pgs.
Shalimov, et al., Intestinal Track Surgery, Kiev, "Dzorovya", 1987, c. 558, 2 pgs.
Notice of Eligibility for Grant of copending Singapore Application No. SG11201500782R, dated Mar. 20, 2017.
Examination Report of copending Singapore Application No. SG11201500782R, dated Mar. 9, 2017, 9 pgs.
Response to Supplementary European Search Report in EP Application No. EP13828055.7, dated Mar. 27, 2017, 14 pgs.
Decision of Grant in Russian Application No. 2015108054, (dated Mar. 15, 2017), 16 pg.
Final Office Action for U.S. Appl. No. 13/963,998 dated Apr. 18, 2017 (16 pgs).
Response to Office Action in Chinese Patent Application No. 2013800523046, filed Apr. 10, 2017, 12 pgs.
Notice of Allowance for U.S. Appl. No. 14/021,720 dated May 16, 2016 (5 pgs).
Response to Office Action dated Nov. 23, 2016 in Canadian Application No. 2880155, dated Apr. 24, 2017.
Response to Further Examination Report of New Zealand Patent Application 704680, dated Jan. 24, 2017, filed Apr. 21, 2017, 22 pgs.
Responses to Final Office Action for U.S. Appl. No. 13/963,998 dated Apr. 18, 2017, filed Jun. 6, 2017 (14 pgs).
Notice of Acceptance of New Zealand Patent Application 704680, dated May 10, 2017, Published on May 26, 2017 in Journal 1655.
Certificate of Grant of copending Singapore Application No. SG11201500782R, dated Jun. 15, 2017.
Publication of Co-Pending Singapore Patent Application No. 10201704073T, Jun. 29, 2017, 1 pg.
Copending U.S. Appl. No. 62/536,364, filed Jul. 24, 2017; first named inventor: C. Kenneth French.
Copending International Patent Application No. PCT/US17/40908 filed Jul. 6, 2017; First Named Inventor: Jesus R. Armenteros.
Singapore Patent Application No. 11201701503Y, Request for Voluntary Amendment filed Aug. 8, 2017.
Copending U.S. Appl. No. 15/642,919, filed Jul. 6, 2017; First-Named Inventor: Moises Jacobs.
U.S. Appl. No. 15/605,812, Non-Final Office Action dated Aug. 7, 2017 (14 pages).
U.S. Appl. No. 13/963,998, Response to Final Office Action with RCE dated Jul. 11, 2017 (12 pgs).
Copending U.S. Appl. No. 15/605,812, filed May 25, 2017; First-Named Inventor: Moises Jacobs.
Freedictionary.com definition of "stretchable", accessed on Aug. 2, 2017, http://www.thefreedictionary.com/stretchable.
U.S. Appl. No. 13/963,998, Non-Final Office Action dated Aug. 21, 2017 (23 pgs).
U.S. Appl. No. 14/836,621, Non-Final Office Action dated Aug. 22, 2017 (16 pgs).
Second Office Action in Chinese Patent Application No. 2013800523046, (dated Jul. 27, 2017), 12 pgs.
Copending U.S. Appl. No. 15/677,227, filed Aug. 15, 2017; First-Named Inventor: Jesús R. Armenteros.
Office Action in Canadian Application No. 2880155, dated Aug. 24, 2017, 14 pgs.
Response to Office Action dated Aug. 24, 2017 in Canadian Application No. 2880155, filed Sep. 27, 2017.
International Search Report and Written Opinion of PCT/US17/40908, dated Sep. 11, 2017.

\* cited by examiner

VERTICALLY ORIENTED BAND FOR STOMACH

CROSS-REFERENCE TO RELATED APPLICATIONS

Pursuant to 35 U.S.C. §120, this application is a continuation of, and incorporates by reference for all purposes, U.S. patent application Ser. No. 11/984,452, entitled "Vertically Oriented Band for Stomach," filed Nov. 19, 2007, and naming Moises Jacobs and Moises Jacobs III as inventors, which is a continuation-in-part of U.S. patent application Ser. No. 11/797,537, entitled "Vertically Oriented Band for Stomach," filed May 4, 2007, and naming Moises Jacobs and Moises Jacobs III as inventors, which claims the benefit of U.S. Provisional Application No. 60/881,138, entitled "Vertically Oriented Band for Stomach," filed Jan. 19, 2007, and naming Moises Jacobs as inventor, all of which are incorporated by reference for all purposes.

BACKGROUND

For patients whose obesity presents an immediate serious health risk, surgical procedures are available to promote weight loss. Two of the most common surgical procedures are gastric bypass and gastric band. During gastric bypass, the stomach is made smaller and food bypasses part of the small intestine. The smaller size stomach causes the patient to eat less and the bypass of the small intestines leads to less calories being absorbed by the body.

In the most common type of gastric bypass surgery, roux-en-y, a small pouch is formed at the top of the stomach using staples. The smaller stomach is connected to the middle portion of the small intestines bypassing the upper portion of the small intestines.

Devices have been developed to form the smaller stomach from the patient's original stomach. One such device is disclosed in U.S. Patent Publication No. 2002/0022851 to Kalloo et al. (Kalloo). Kalloo discloses a loop 80 reducing the volume of the gastric cavity. A feeder line is pulled to reduce the diameter of the loop and collapse the walls of the stomach to define a smaller pouch.

U.S. Patent Publication No. 2006/0157067 to Saadat et al. (Saadat) discloses the use of tissue anchors to form a gastric pouch acting as a restriction to the passage of fluids and food. U.S. Pat. No. 5,345,949 to Shlain (Shlain) discloses a clip placed across the fundus of the stomach to restrict the inlet chamber or proximal pouch. Likewise, U.S. Pat. No. 6,869,438 to Chao (Chao) discloses a gastric partitioning clip creating a stomach pouch from the stomach to restrict the amount of food intake.

It is an object of the invention to provide a device for separating the stomach into two compartments but allowing communication between the compartments.

It is another object of the invention to provide a device for forming a smaller stomach pouch, the size of the pouch being tailored to the patient's individual circumstances.

It is another object of the invention to provide a procedure creating a small stomach pouch to limit intake of food separate from the stomach but allowing gastric juices from the excluded stomach to flow into the pouch.

It is still another object of the invention to provide a system for creating a small pouch from the main stomach that is reversible.

It is still another object of the invention to alter the production of hormones, enzymes and chemicals that affect metabolism, energy levels, hunger, digestion, absorption of nutrients, weight loss, maintenance or gain that may be affected by exclusion of the gastric fundus and body of the stomach.

These and other objects of the invention will become apparent after reading the disclosure of the invention.

SUMMARY

An adjustable band or clamp or non-adjustable clamp is placed about the greater curvature of the stomach in a vertical orientation. The band or clamp completely compartmentalizes the stomach between a small vertical pouch and the fundus and body of the stomach. The fundus and body of the stomach are excluded from nutrients and are separated from a long narrow channel where the food travels. A small passage at the level of the antrum allows gastric juices to empty from the fundus and body of the stomach. The clamp may be applied during open surgery in laproscopic surgery or using a single port technique, or through any natural orifice in NOTES (Natural Orifice Transluminal Endoscopic surgery) or using a hybrid surgical technique.

DETAILED DESCRIPTION OF THE DRAWINGS

Figure 1:
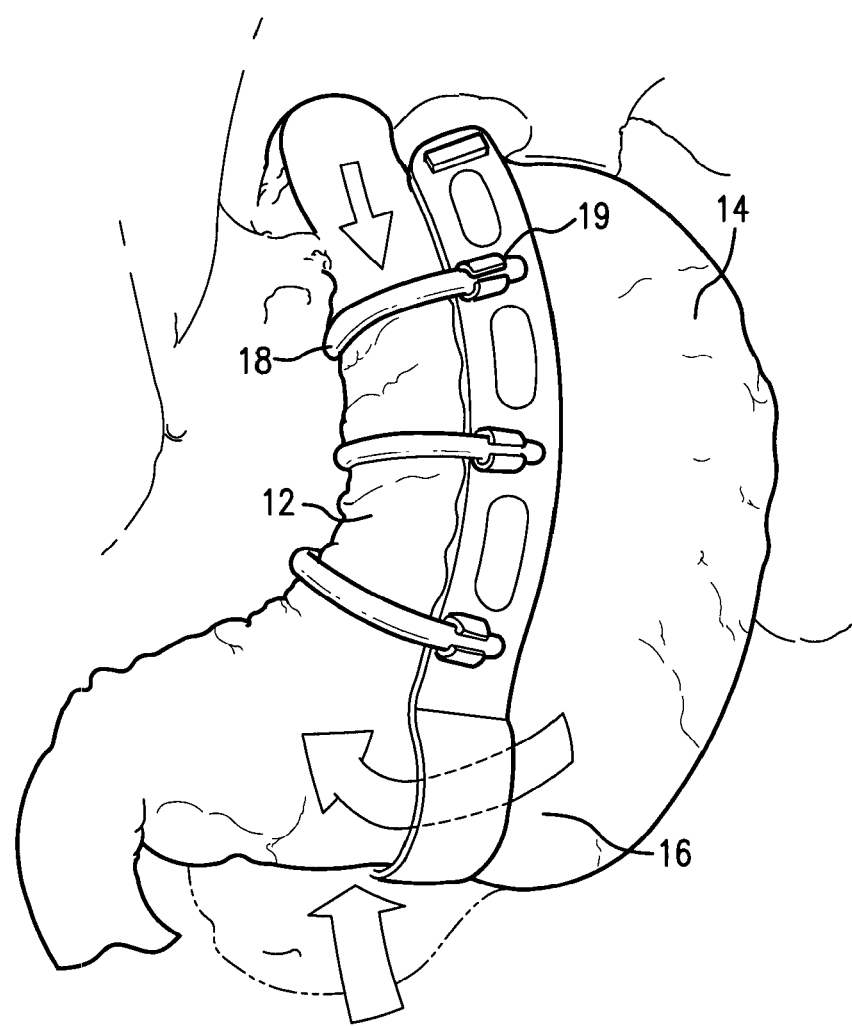
FIG. 1 is a view of the band applied to a stomach.

In FIG. 1, a stomach having the band 10 applied can be seen dividing the stomach into the pouch 12 and fundic and body area 14. Food traveling down the esophagus enters the pouch 12 and exits into the antrum. The band 10 applies pressure against the sides of the stomach to separate the stomach into the two compartments, but does not apply pressure to the stomach walls at the bottom part of the stomach. This creates a passage 16 allowing flow of gastric juices from the fundic and body area 14 into the antrum. Food will not enter the fundic and body of the stomach through this passage, however. At least one horizontal strap 18 may be used to secure the band in place. The straps may be adjustable and may apply pressure sufficient to impact the size and function of the pouch 12.

Figure 2:
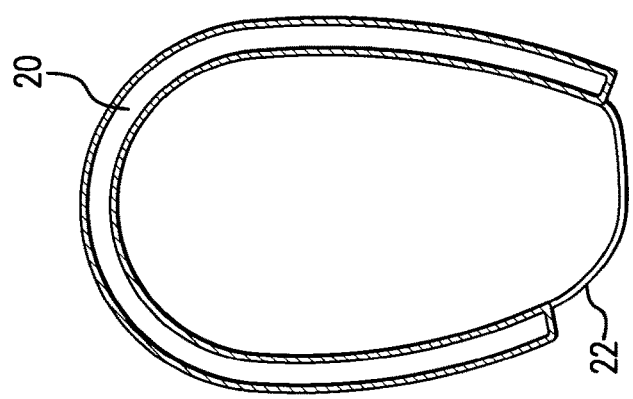
FIG. 2 is a cross-sectional view of an inflatable clamp useable with the invention.

FIG. 2 shows an embodiment of the clamp having an inflatable chamber 20 and a connecting section 22. The clamp is placed about the stomach in a vertical orientation to separate the stomach into the two compartments and inflated. The clamp may have an asymmetrically placed chamber 20, that when inflated applies pressure on the stomach to seal the two compartments from one another except for the passage 16. The connecting section 22, being not inflated, does not apply pressure to the bottom portion of the stomach, allowing for the formation of the passage 16. In addition, the clamp may have an asymmetrically placed inflatable chamber that faces the lesser curvature side of the stomach, that when inflated or deflated only alters the lumen of the vertical compartment through which the nutrients pass and does not play a role in the creation of the two compartments.

Figure 3:
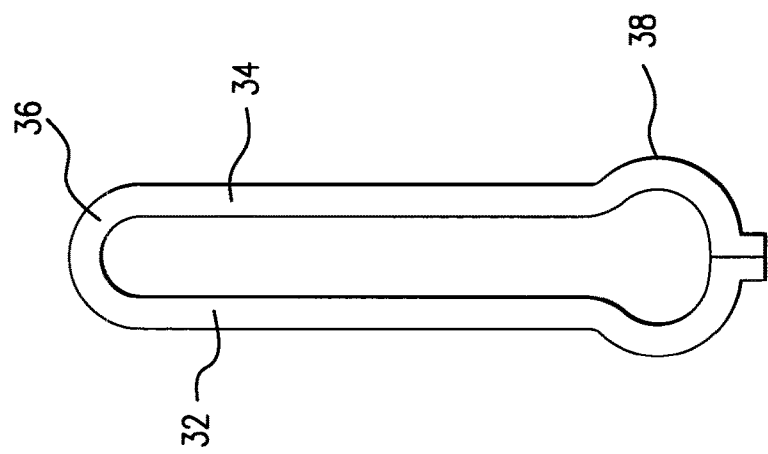
FIG. 3 is a view of a non-adjustable clamp used with the invention.

FIG. 3 shows the rigid clamp embodiment having a U portion formed by two legs 32, 34 connected by a bight portion 36. When the clamp is placed on the stomach, the bight portion 36 fits over the top of the stomach with the legs 32, 34 applying enough pressure to collapse the walls of the stomach against one another to create the two compartments. The legs 32, 34 may or may not extend the full vertical extent of the stomach to allow for the creation of the passage 16. The legs are attached by a connector 38. When applied to the stomach, the legs serve to push the sides of the stomach together to form a complete seal but the connector allows for the formation of a passage between the two compartments. The clamp may be adjustable. The legs of the clamp may be made or adjusted to any length depending on the size of the stomach the legs can be made shorter or longer. The two legs may be connected by a magnetic coupler rather than a solid bight portion but may not be connected at all at the proximal end of the stomach. The apposition of the clamp legs about the stomach must be accomplished without sufficient force to cause ischemia of the gastric walls when the legs are closed.

Besides a clip, the vertical band may be formed as or with an inflatable balloon, as discussed with reference to FIG. 2. The orientation of the balloon is such that, upon inflation, the balloon bulges to the left to decrease the size of the compartment 12. The bottom portion may or may not be inflatable. The balloon may be attached to a tube exiting the body so that the balloon may be adjusted without the need for invasive surgery.

Figure 4:
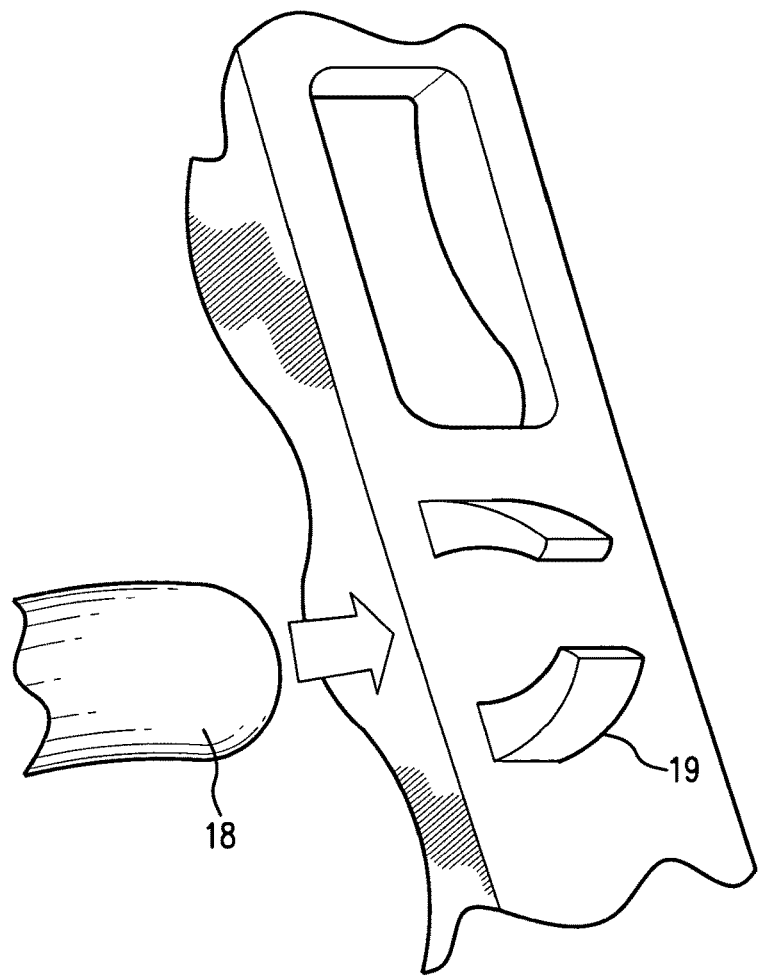
FIG. 4 is a detailed view of the strap attachment to the band.

Straps 18 can be secured to the band in any number of conventional ways. One possible way in which to secure the straps to the band is depicted in FIG. 4. The band engages and is secured by clips 19 which extend outwardly from the band. This arrangement allows the straps to be tightened by being pulled through the clip and, if desired, the straps can be released for the removal of the band. These straps may also have an inflatable chamber and may be adjustable so as to also increase or decrease the lumen of the vertical compartment through which the nutrients pass.

Figure 5:
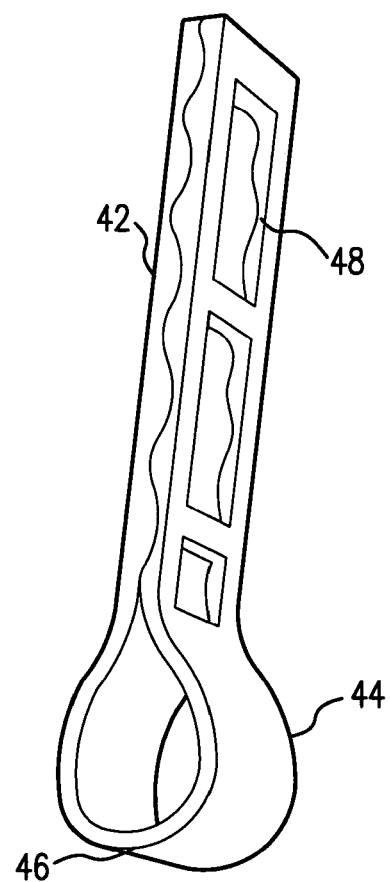
FIG. 5 is a perspective view of a second embodiment of the band.

An alternative construction of the band is seen in FIG. 5. In this embodiment, the band has a first section 42 having two parallel arms and a second section with two space members so that, when applied to a stomach, the passageway 16 is formed. The clamp itself may be curved to allow for better accommodation about the lesser curvature. The arms may be straight, curved or undulating. The surface may be smooth or serrated. The arms of the first section 42 are resiliently biased against one another and are spaced from one another in order that, when applied, the first section maintains the walls of the stomach together to separate the stomach into the first and second compartments. The pressure applied must be enough that the two compartments are formed but not so much that the walls of the stomach are damaged or compromise the blood supply. The section 44 is connected together by a section 46 acting as a hinge. This allows the arms of the first section 42 to be separated from one another in order that the band may be applied. Conversely, it is possible to have the two arms of the first section 42 hinged to one another and the two arcuate portions forming the second section 44 not connected to one another.

Figure 6:
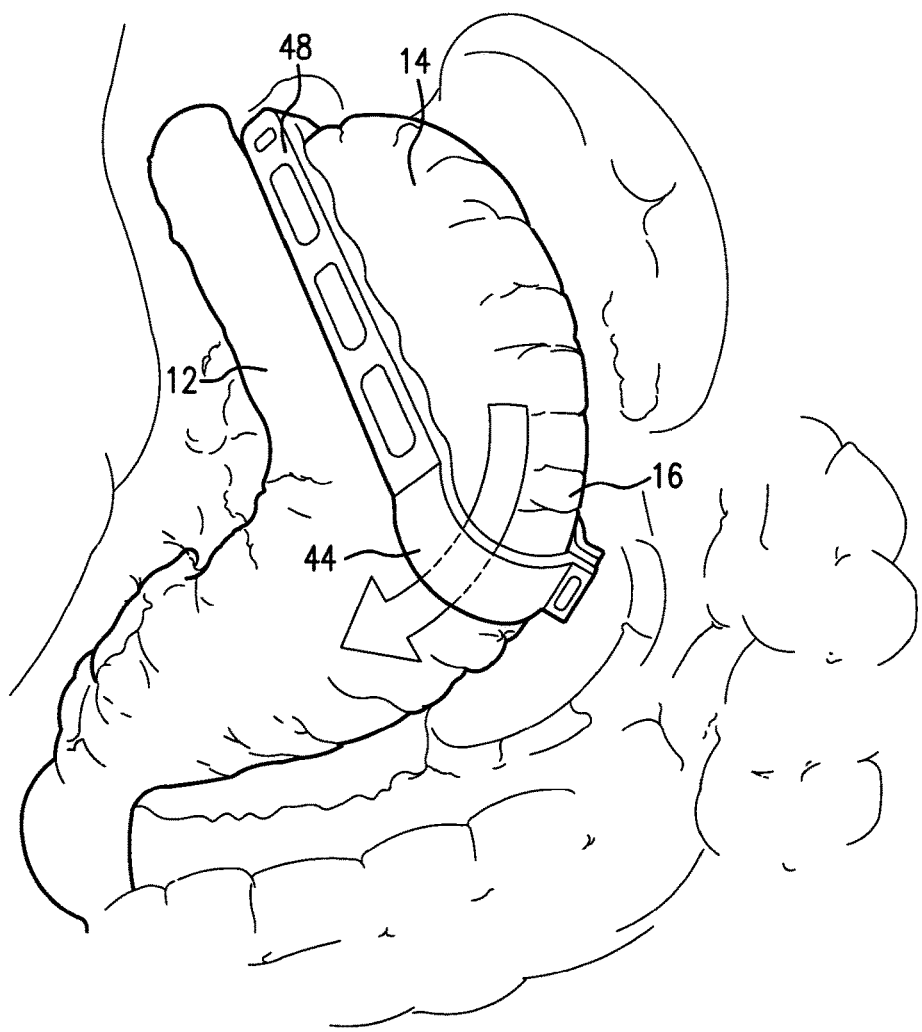
FIG. 6 is a view of the band in FIG. 5 applied to a stomach.

The band of FIG. 5 applied to stomach is seen in FIG. 6. Seen here as the first section 42 extending along the stomach to separate the stomach into two compartments, including pouch 12 and fundic and body area 14, whereas the second section has arcuate arms forming a passage 16. At least one of the arms of the first section is provided with apertures 48. The apertures, which may be large or small, allow part of the stomach wall to enter the aperture to help prevent movement of the band once it has been applied.

There are many ways in which the clamp can be applied including Natural orifice transluminal endoscopic surgery (NOTES) and the combination of NOTES and an assistant trochar placed in to the abdominal cavity. Combinations include any combination of the conventional, laproscopic, NOTES and one port techniques. The NOTES technique includes transgastric, transvaginal, transrectal, transcolonic and combinations of these. Another possibility is the one port technique wherein one port is used for the introduction of several instruments. The one port technique encompasses a one port abdominal (including umbilical), perineal, retroperitoneal approaches and combinations of these.

To facilitate application of the band, a bougie may be utilized in any suitable manner, such as placed transorally, transgastrically or transintestinally. The bougie, having a vacuum suction apparatus, collapses the stomach wall to align and help the placement the clamp. To help with alignment and placement of the clamp, the bougie may have magnets to mate with the magnets or metallic areas when the clamp is provided with such. Also, the band may be made of bioabsorbable material to negate the need to remove it.

While the invention has been described with reference to preferred embodiments, various modifications would be apparent to one of ordinary skill in the art. The invention encompasses such variations and modifications.

What is claimed is:

1. A gastric band configured to partition a stomach into a first portion and a second portion, and to provide a passage between the first and second portions of the stomach, the gastric band comprising:

a partitioning section comprising a distal end of the gastric band and configured to extend from a first end of the stomach towards a second end of the stomach opposite the first end, the partitioning section having a first arm extending a majority of a length of the gastric band and a second arm extending a majority of the length of the gastric band and spaced apart from the first arm by a first distance configured to partition the stomach into the first and second portions; and a passage-forming section comprising a proximal end of the gastric band, the passage-forming section configured to extend from the second end of the stomach towards the first end of the stomach, the passage-forming section configured to form the passage between the first and second portions of the stomach, the passage-forming section having first and second passage-forming arms extending substantially in a direction towards the partitioning section and at least partially spaced apart at a first location by a second distance greater than the first distance;

wherein the first and second passage-forming arms are continuous with each other and are both at least partially curved, the first passage-forming arm is continuous with the first arm of the partitioning section, and the second passage-forming arm is continuous with the second arm of the partitioning section, wherein the first passage-forming arm is substantially collinear with the first arm of the partitioning section when viewed from at least one angle, and wherein the second passage-forming arm is substantially collinear with the second arm of the partitioning section when viewed from at least one angle.

2. The gastric band of claim 1, wherein the first portion of the stomach is a food pouch and the second portion of the stomach is a fundic region.

3. The gastric band of claim 1, wherein the first and second arms of the partitioning section are parallel.

4. The gastric band of claim 1, further comprising apertures in at least one of the first or second arms of the partitioning section.

5. The gastric band of claim 1, wherein the first and second passage-forming arms are symmetrically disposed.

6. The gastric band of claim 1, further comprising a biasing section configured to bias at least the first and second arms of the partitioning section to form the first and second portions of the stomach.

7. The gastric band of claim 6, wherein the biasing section is further configured to bias the first and second passage-forming arms to form the passage between the first and second portions of the stomach.

8. The gastric band of claim 6, wherein the biasing section is disposed towards the distal end of the gastric band.

9. The gastric band of claim 6, wherein the biasing section is disposed towards the proximal end of the gastric band.

10. The gastric band of claim 6, wherein the biasing section comprises at least one of a hinge, bight portion, and magnetic coupler.

11. The gastric band of claim 1, wherein the gastric band further comprises at least one strap coupled to the first and second arms of the partitioning section.

12. The gastric band of claim 1, further comprising an inflatable portion.

13. The gastric band of claim 12, wherein the inflatable portion comprises at least a portion of the partitioning section.

14. A gastric band, comprising:
  a first section having first and second arms spaced from one another a first distance configured to close walls of a stomach together to form a first compartment of the stomach and a second compartment of the stomach, said first section extending a majority of a length of said gastric band; and
  a second section disposed at an end of the gastric band opposite the first section, the second section having a first arm substantially collinear with the first arm of the first section when viewed from at least one angle, and having a second arm substantially collinear with the second arm of the first section when viewed from at least one angle, the first and second arms of the second section being at least partially spaced from one another a second distance configured to form a passage between the first compartment of the stomach and the second compartment of the stomach, wherein the second distance is greater than the first distance;
  wherein the first and second arms of the second section are continuous with each other and are both at least partially curved, the first arm of the second section is continuous with the first arm of the first section, and the second arm of the second section is continuous with the second arm of the first section.

15. The gastric band of claim 14, wherein the first compartment of the stomach comprises a food pouch and the second compartment of the stomach comprises a fundic region.

16. The gastric band of claim 14, wherein the passage formed by the second section provides a passage from the second compartment into an antrum of the stomach.

17. The gastric band of claim 14, further comprising a biasing section configured to bias at least the first and second arms of the first section to form the first and second compartments of the stomach.

18. The gastric band of claim 14, further comprising a biasing section configured to bias at least the first and second arms of the second section to form the passage between the first compartment of the stomach and the second compartment of the stomach.

19. The gastric band of claim 14, further comprising an inflatable portion.

20. The gastric band of claim 19, wherein the inflatable portion comprises at least a portion of the first section.

* * * * *